United States Patent [19]

Davidson et al.

[11] Patent Number: 5,674,280
[45] Date of Patent: Oct. 7, 1997

[54] VALVULAR ANNULOPLASTY RINGS OF A BIOCOMPATIBLE LOW ELASTIC MODULUS TITANIUM-NIOBIUM-ZIRCONIUM ALLOY

[75] Inventors: James A. Davidson, Collierville, Tenn.; Kenneth P. Daigle, Olive Branch, Miss.

[73] Assignee: Smith & Nephew, Inc., Memphis, Tenn.

[21] Appl. No.: 542,513

[22] Filed: Oct. 12, 1995

Related U.S. Application Data

[63] Continuation-in-part of Ser. No. 112,599, Aug. 26, 1993, Pat. No. 5,477,864, which is a continuation-in-part of Ser. No. 36,414, Mar. 24, 1993, Pat. No. 5,509,933, which is a continuation-in-part of Ser. No. 986,280, Dec. 7, 1992, abandoned, which is a continuation-in-part of Ser. No. 647,453, Jan. 28, 1991, Pat. No. 5,169,597, which is a continuation of Ser. No. 454,181, Dec. 21, 1989, abandoned.

[51] Int. Cl.⁶ ..................................................... A61F 2/24
[52] U.S. Cl. ................................................................ 623/2
[58] Field of Search .................................. 623/1, 2.3, 11, 623/66; 148/133, 421, 669

[56] References Cited

U.S. PATENT DOCUMENTS

| | | | |
|---|---|---|---|
| 2,892,706 | 4/1959 | Jafee et al. . | |
| 2,987,352 | 5/1961 | Watson . | |
| 3,370,946 | 2/1968 | Bertea et al. . | |
| 3,408,604 | 10/1968 | Toshio Doi et al. | 335/216 |
| 3,643,658 | 2/1972 | Steinemann . | |
| 3,677,795 | 7/1972 | Bokros et al. . | |
| 3,752,664 | 8/1973 | Steinemann | 420/417 |
| 3,777,346 | 12/1973 | Steinemann . | |
| 3,849,124 | 11/1974 | Villani | 420/417 |
| 3,906,550 | 9/1975 | Rostoker et al. . | |
| 3,911,783 | 10/1975 | Gapp et al. | 420/417 |
| 4,040,129 | 8/1977 | Steinemann et al. | 148/11.5 |
| 4,145,764 | 3/1979 | Suzuki et al. . | |
| 4,170,990 | 10/1979 | Baumgart et al. | 606/78 |
| 4,197,643 | 4/1980 | Burstone et al. | 420/421 |
| 4,511,411 | 4/1985 | Brunner et al. . | |
| 4,857,269 | 8/1989 | Wang et al. | 420/417 |
| 4,902,359 | 2/1990 | Takeuchi et al. | 148/133 |
| 4,983,184 | 1/1991 | Steinemann | 623/66 |
| 5,169,597 | 12/1992 | Davidson et al. | 428/613 |

FOREIGN PATENT DOCUMENTS

| | | |
|---|---|---|
| 0 437 079 A1 | 12/1990 | European Pat. Off. . |
| 2703529 | 8/1978 | Germany . |

OTHER PUBLICATIONS

Zwicker, et al., Z. Metallkunde, 61 (1970) pp. 836–847.
Collings, E.W., "The Physical Metallurgy of Titanium Alloys," *American Society for Metals*, pp. 40–41, 66–69, 72–73, 120–121, 190–191, 194–195, 214–215, 218–219, 226–227 (No Date).
Collings, E.W., "The Physical Metallurgy of Titanium Alloys," *American Society for Metals*, pp. 68–70 (No Date).
Albert, et al., Z. Metallunde, 62 (1972) 126.
Brown & Merritt, "Evaluation of Corrosion Resistance of Biology," Case Western Reserve University, 13 Feb. 1986 (1:8).

(List continued on next page.)

*Primary Examiner*—David Isabella
*Attorney, Agent, or Firm*—Pravel, Hewitt, Kimball & Krieger

[57] ABSTRACT

An annuloplasty ring of low elastic modulus Ti—Nb—Zr alloy to provide enhanced biocompatibility, hemocompatibility, flexibility and strength. Components of the annuloplasty ring can be surface hardened by oxygen or nitrogen diffusion or by depositing a tightly adherent, hard, wear-resistant, hemocompatible ceramic coating by physical vapor deposition and chemical vapor deposition. The Ti—Nb—Zr alloy can be used as a fabrication material for any annuloplasty ring component that either comes into contact with blood, thereby demanding high levels of hemocompatibility, or that is subject to microfretting, corrosion, or other wear such that a low elastic modulus metal with a corrosion-resistant, hardened surface would be desirable.

19 Claims, 2 Drawing Sheets

OTHER PUBLICATIONS

Mears, "Electron–Probe Microanalysis of Tissue and Cells from Implant Areas," *Jnl of Bone and Joint Surgery*, vol. 48B, No. 3, pp. 576–76 (Aug. 1966).

Ferguson, Liang, and Hodge, "The Ionization of Metal Implants in Living Tissues" *Jnl of Bone and Joint Surgery*, vol. 42A, No. 1, pp. 77–90 (Jan. 1960).

Hoar and Mears, "Corrosion–Resistant Alloys in Chloride Solutions: Materials for Surgical Implants," pp. 506–507.

Kirk–Othmer Encyclopedia of Chemical Technology, vol. 23, pp. 98–113.

Jepson, et al., The Science & Tech., Titanium ed. Jaffee, et al., Pergamon, N.Y., 1968, p. 677.

Heller, et al., Jour. Less Common Metals, 24 (1971) 265.

Van Noort, R., Jour. Mat. Sci., 22 (1987) 3801.

The Japan Medical Review, vol. 12, (Undated) unumbered page, pp. 12, 23.

Author Unknown, "Titanium–Niobium Base Quaternary Alloys," (Date Unknown), pp. 405–419.

VALVULAR ANNULOPLASTY RINGS OF A BIOCOMPATIBLE LOW ELASTIC MODULUS TITANIUM-NIOBIUM-ZIRCONIUM ALLOY

RELATED APPLICATIONS

This application is a continuation-in-part of U.S. Ser. No. 08/112,599 filed Aug. 26, 1993, now U.S. Pat. No. 5,477,864, which is in turn a continuation-in-part of U.S. Ser. No. 08/036,414, filed Mar. 24, 1993, now U.S. Pat. No. 5,509,933, which is in turn a continuation-in-part of U.S. Ser. No. 07/986,280 filed Dec. 7, 1992 and now abandoned, which is in turn a continuation-in-part of U.S. Ser. No. 07/647,453, filed Jan. 28, 1991 and now U.S. Pat. No. 5,169,597, which is in turn a continuation of U.S. Ser. No. 07/454,181, filed Dec. 21, 1989, now abandoned.

BACKGROUND OF THE INVENTION

1. Field of the Invention

This invention relates to valvular annuloplasty ring prostheses. In particular, the invention relates to valvular annuloplasty ring prostheses constructed of a biocompatible low elastic modulus titanium-niobium-zirconium alloy that provides enhanced biocompatibility, hemocompatibility and flexibility. The valvular annuloplasty ring prostheses can optionally be surface hardened to form a wear resistant, inert, ceramic oxide surface layer.

2. Description of the Related Art

Valvular annuloplasty is a procedure for correcting deformities of the natural valves of the heart through implantation of a prosthesis, typically ring-shaped, which restores the shape of the deformed valve. Valvular annuloplasty is often utilized for correcting the tricuspid or mitral valves, although it is not restricted to those valves. Surgical alternatives to annuloplasty include replacement of the heart valve with a biological tissue valve or a mechanical valve.

Typical current annuloplasty rings are formed of a solid core, constructed from either a polymeric or metallic substance, and a woven polymeric sleeve or sheath, encasing the core. For example, U.S. Pat. No. 3,656,185 to Carpentier describes a ring core of stainless steel with a stitchable cord of polytetraflourethylene, both encased in a textile sheath and U.S. Pat. No. 4,055,861 to Carpentier et al. describes an annuloplasty ring core constructed of a flexible biocompatible material enclosed in a textile sheath. U.S. Pat. No. 5,104,407 to Lam et al. describes a ring core made of a biocompatible material that is also antimagnetic, such as a cobalt-nickel alloy, with a knit polymeric outer sheath.

As with any surgical procedure, valvular annuloplasty faces complications that include malfunction of the ring due to distortion of the implant, physical or chemical deterioration of ring components, and tearing of the typical cloth sheath. The biocompatibility and physical characteristics (such as elasticity, strength, and wear resistance) of materials used in the annuloplasty ring components can be a factor in some of these complications.

Additionally, polymeric materials used in valvular annuloplasty constructs can degrade with time in the body. Water absorption and oxidation of the polymeric material can also adversely affect the material's properties, which can in turn lead to physical and structural alteration of the annuloplasty ring and adverse biological responses.

Metallic rings can experience damage of natural passive surface oxides via local movement of tissue or the sewing sleeve. This local movement can produce metal ions, debris, and micro-electric currents which can adversely alter protein, tissue, platelet, and other cell attachments to the ring. Relatively high elastic modulus, and thus low flexibility, of the typical metals used to construct annuloplasty ring cores, such as pure titanium, can lead to less than ideal mechanical performance.

In an annuloplasty ring where the core is fabricated from a metallic element and the sewing ring (also referred to as a sleeve or sheath) is a polymer, there exists the possibility of metal ion release and micro-electrical (galvanic related) circuits due to abrasion between the polymeric sheath and metal core. The effect of metal ions and micro-electrical circuits on a biological environment is not entirely understood but it has been linked to adverse cellular, platelet, and protein response and the need for implant replacement.

There still exists a need for valvular annuloplasty ring prostheses that are fabricated from a lightweight, biocompatible, and blood and tissue compatible material, that is readily formable into complex shapes and which can be optionally surface hardened to provide resistance to abrasive wear, microfretting wear, and the corrosive effects of body fluids.

SUMMARY OF THE INVENTION

The present invention provides valvular annuloplasty rings, for implantation in living body tissue of a patient, which are fabricated from a low elastic modulus, biocompatible, hemocompatible titanium alloy with niobium and optionally zirconium. The inventive titanium alloy is substantially free of toxic elements, such as aluminum, manganese, vanadium, cobalt, nickel, molybdenum and chromium, except such amount of the toxic elements as may occur as impurities in the alloy and as contaminants as a result of processing the alloy. These amounts of impurities and contaminants are too insignificant to cause adverse effect on the patient's body. The present invention also provides surface hardened annuloplasty rings produced by oxygen or nitrogen diffusion. The hardened surfaces are corrosion resistant, biocompatible and have improved resistance to wear.

The inherently low elastic modulus of Ti—Nb—Zr alloys, between about 6 million and about 12 million psi depending on metallurgical treatment and composition, provides a flexible and forgiving material for use in the fabrication of components of an annuloplasty ring, which are generally a core and a woven sleeve.

The use of a titanium-niobium-zirconium alloy in annuloplasty ring components enhances biocompatibility, hemocompatibility, flexibility and strength of the annuloplasty ring. In addition, the unique ability of this alloy to form a hard, dense, inert, and abrasion and corrosion resistant surface oxide upon controlled elevated-temperature oxidation provides an annuloplasty ring with a unique resistance to surface degradation.

BRIEF DESCRIPTION OF THE DRAWINGS

A better understanding of the present invention can be obtained when the detailed description of the preferred embodiments is considered in conjunction with the following drawings, in which.

DETAILED DESCRIPTION OF THE PREFERRED EMBODIMENTS

Figure 1:
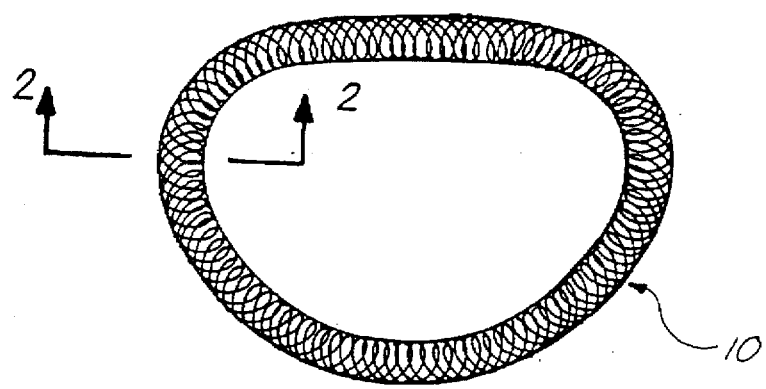
FIG. 1 is a schematic representation of an annuloplasty ring, which is commercially available under the trademark (CARPENTIER-EDWARDS PHYSIO) from Baxter Healthcare, Irvine, Calif.

The preferred titanium alloys for use in the present invention have the compositions: (i) titanium, and from about 10 wt. % to about 20 wt. % niobium; and (ii) titanium, and from about 35 wt. % to about 50 wt. % niobium. In either composition, zirconium can be included in an amount sufficient to retard the transformation of beta. A preferred amount of zirconium is up to 20 wt. %. Tantalum can be present as a substitute for niobium to stabilize beta-phase titanium, however niobium is the preferred component due to its effect of lowering the elastic modulus of the alloy when present in certain specific proportions.

Other elements, such as aluminum, manganese, vanadium, cobalt, nickel, molybdenum and chromium, are not deliberately added to the alloy but can be present in insignificant quantities that occur as impurities in the commercially pure titanium, niobium, zirconium or tantalum used to prepare the alloy and as may arise from the alloying process. The exclusion of elements besides titanium, niobium, zirconium or tantalum results in alloys which are substantially free of known carcinogens or elements that are known or suspected of inducing diseases or adverse tissue responses.

From hereinafter in this specification, these inventive alloys are referred to as "Ti—Nb—Zr alloys" or as "titanium alloys," even though tantalum may also be present, zirconium may not be present in the alloy composition, and the titanium portion of the alloy may be less than 50 wt. %.

Without the presence of zirconium in the composition, the ability of the titanium alloy to be surface hardened by oxygen or nitrogen diffusion is limited. Therefore, the presence of zirconium, in amounts ranging from about 0.5 to about 20 wt. %, is preferred when the alloy is to be diffusion hardened. The most preferred alloy includes about 74 wt. % titanium, about 13 wt. % niobium and about 13 wt. % zirconium.

U.S. Pat. No. 5,169,597 to Davidson et al. and U.S. patent application Ser. No. 08/112,599, both of which are hereby fully incorporated by reference, describe in more detail the satisfactory compositions of the Ti—Nb—Zr alloys. In addition, U.S. Ser. No. 08/036,414, hereby fully incorporated by reference, describes how to hot-work Ti—Nb—Zr alloys to produce high strength, low modulus prostheses.

Cold-working of the Ti—Nb—Zr alloys useful in the invention can reduce stiffness (elastic modulus) significantly and increases strength while maintaining biocompatibility and corrosion resistance properties. For example, when the alloy is in a predominantly hexagonal close-packed crystal structure it can be cold worked up to about 90%, but cold working to between about 30% and about 60% is preferred in order to reduce stiffness (elastic modulus) and improve the strength of the alloy while retaining good ductility and corrosion resistance.

The % cold work is defined as $(\Delta A/A_0) \times 100$, where $\Delta A$ is the change in cross-sectional area and $A_0$ is the initial cross-sectional area. Cold working can be carried out by processes such as drawing, forging, stamping, rolling, extruding, rotary swaging and the like to achieve a high degree of elastic toughness. The cold working process is preferably performed at room temperature, but can also be performed at temperatures up to about 300° C.

Components of the inventive annuloplasty rings can be surface hardened by depositing a hard wear resistant coating on the components' surfaces, so as to provide an electrically insulative film and/or to reduce wear between an annuloplasty ring core and sleeve. An amorphous diamond-like carbon coating or a ceramic like coating, such as zirconium or titanium oxide, zirconium or titanium nitride, or zirconium or titanium carbide, can be deposited on component surfaces by using chemical vapor deposition and physical vapor deposition.

Alternatively and more preferably, the components of the inventive annuloplasty rings can be surface hardened by oxygen diffusion or nitrogen diffusion. A preferred method for oxygen diffusion surface hardening is described in U.S. Pat. No. 5,372,660 to Davidson et al., which is hereby fully incorporated by reference.

Oxygen diffusion according to U.S. Pat. No. 5,372,660 requires the provision of oxygen, an oxygen containing atmosphere, or compounds partially composed of oxygen, such as water (steam), carbon dioxide, nitrogen dioxide, sulfur dioxide, and the like to the surfaces of the annuloplasty ring component to be surface hardened, while the component is maintained at a predetermined temperature. The preferred temperature is between about 200° C. and about 1200° C. The amount of time required at a given temperature to effectively produce the surface and near-surface hardened components is related exponentially, by an Arhennius-type relationship, to the temperature. That is, shorter periods of time are required at higher temperatures for effective diffusion hardening. In a most preferred surface hardened embodiment, the Ti—Nb—Zr alloy is subjected to a temperature and an environment of argon gas, that has been moisturized by bubbling through a water bath. The water vapor disassociates at the component surface to produce oxygen, which diffuses into the component to yield the desired hardened surface. Conventional methods of oxygen surface hardening are also useful.

In nitrogen diffusion, nitrogen sources are supplied instead of oxygen. Nitrogen diffusion hardens the titanium alloy in a similar manner as oxygen diffusion. Nitridation, commonly known in the art, can also be used to achieve a hard nitride layer.

Either hardened or non-hardened surfaces of the inventive annuloplasty ring components can be coated with medicaments, such as anti-inflammatory agents, antithrombogenic agents, antibiotics, antimicrobial agents, anticoagulants, and proteins that reduce platelet adhesion, in order to further improve the biocompatibility of the components.

Deposition of silver or boron film on the annuloplasty ring component surfaces, hardened or non-hardened, reduces friction and wear. By ion-beam assisted silver deposition, up to about 3 micron thick silver films can be deposited on the component surfaces at room temperature in a vacuum chamber equipped with an electron-beam silver evaporation source. A mixture of argon and oxygen gas is fed through the ion source to create an ion flux. An example of satisfactory operation parameters can be shown by an acceleration voltage of 1 kev with an ion current density of 25 microamps per $cm^2$. The desired thickness of the silver film can be deposited in its entirety by this ion bombardment or partially via bombardment with the remainder being deposited by vacuum evaporation. Ion bombardment improves the attachment of the silver film to the Ti—Nb—Zr alloy.

Boronation of the component surfaces can be achieved by, for example, commercially available boride vapor deposition, boron ion implantation, sputter deposition using standard ion implantation and evaporation, or spontaneous formation of boron film in air. Boric acid ($H_3BO_3$) films, which provide the component surfaces with a self-replenishing solid lubricant, are formed from the reaction of the $B_2O_3$ surface (deposited by various conventional methods) on the component surface with the water present in the body of the recipient-patient. Conventional methods that can be employed to deposit either a boron, $H_3BO_3$, or $B_2O_3$ film on the annuloplasty ring component surface include vacuum evaporation (with or without ion bombardment) and simple oven curing of a thin layer over the implant surface. The self-lubricating mechanism of $H_3BO_3$ is governed by its unique layered, triclinic crystal structure which allows sheets of atoms to easily slide over each other during movement, thus minimizing component wear and friction.

Figure 2:
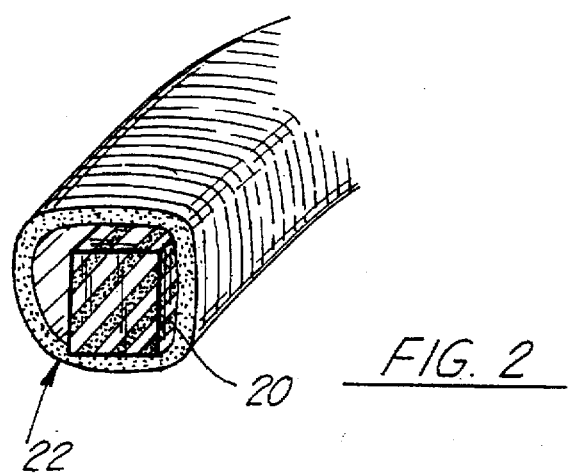
FIG. 2 is a cross-sectional diagram of the ring in FIG. 1 along the plane A—A.

FIG. 1 shows a valvular annuloplasty ring construct 10. Valvular annuloplasty ring construct 10 is shown in cross-section in FIG. 2 and includes an inner core component 20 and an encasing woven sleeve component 22. An inventive annuloplasty ring embodiment of this type of construction would have the core 20 at least partially fabricated of Ti—Nb—Zr alloy.

In another preferred embodiment of the inventive annuloplasty ring, the core 20 would be at least partially fabricated from oxygen diffusion surface hardened Ti—Nb—Zr alloy.

In another preferred embodiment of the inventive annuloplasty ring, the core 20 is at least partially fabricated from surface oxidized Ti—Nb—Zr encased in sleeve 22 woven from wire fabricated of a surface oxidized Ti—Nb—Zr alloy.

Yet another preferred embodiment of this type of construction is an annuloplasty ring core component 20 fabricated from cold-worked Ti—Nb—Zr alloy encased in a sleeve component 22 woven from wire fabricated of surface oxidized, and thus hardened, Ti—Nb—Zr alloy. This embodiment takes advantage of the extremely low elastic modulus characteristics of these alloys in the cold-worked condition and allows for design flexibility in creating annuloplasty rings with varying deformation characteristics.

Figure 3:
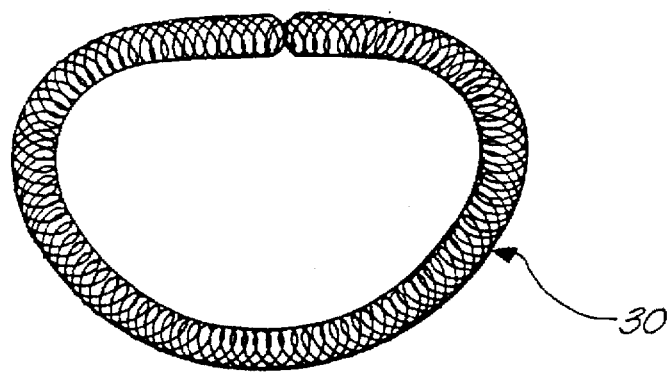
FIG. 3 is a schematic representation of a tricuspid annuloplasty ring sold under the trademark (CARPENTIER-EDWARDS) by Baxter Healthcare.
Figure 4:
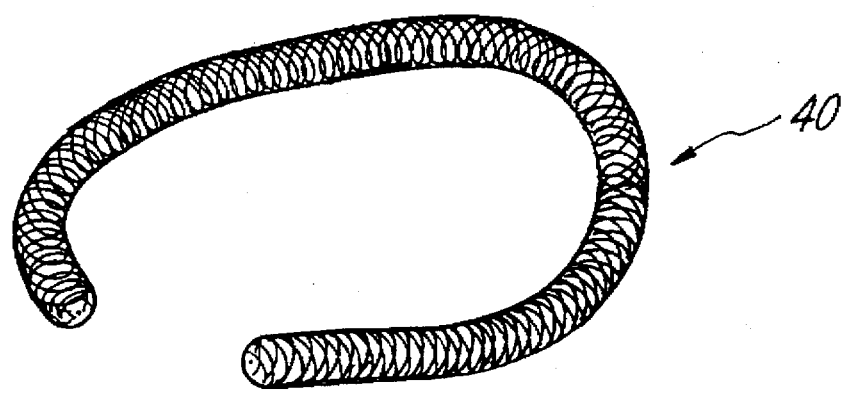
FIG. 4 is a schematic representation of a mitral annuloplasty ring sold under the trademark (CARPENTIER-EDWARDS) by Baxter Healthcare.
Figure 5:
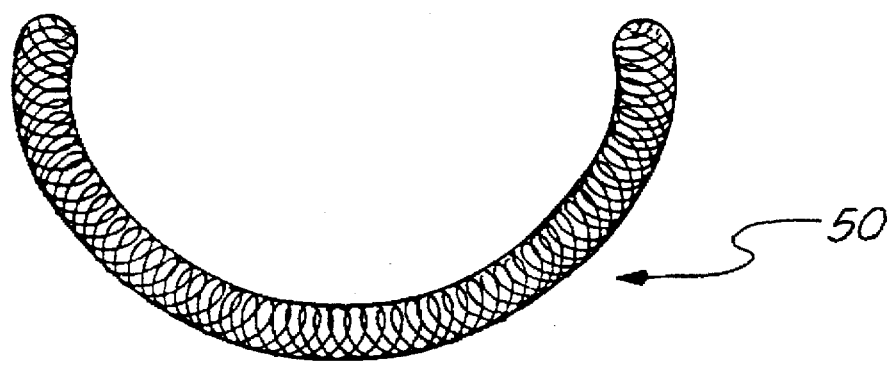
FIG. 5 is a schematic representation of another annuloplasty ring sold under the trademark (COSGROVE EDWARDS) by Baxter Healthcare.

FIG. 3 shows a tricuspid annuloplasty ring construct 30, FIG. 4 a mitral valve ring construct 40, and FIG. 5 yet another annuloplasty ring construct 50, components of which can also be constructed of the Ti—Nb—Zr alloy.

The invention is, of course, not limited in its application to the annuloplasty constructs of FIGS. 1-5 but includes all suitable annuloplasty rings.

Although the invention has been described with reference to its preferred embodiments, those of ordinary skill in the art may, upon reading this disclosure, appreciate changes and modifications which may be made and which do not depart from the scope and spirit of the invention as described above and claimed below.

What is claimed is:

1. An annuloplasty ring for implantation in living body tissue of a patient, the annuloplasty ring having enhanced biocompatibility, comprising:
   components at least partially fabricated from a metal alloy comprising:
   (i) titanium; and
   (ii) from about 10 to about 20 wt. % niobium or from about 35 to about 50 wt. % niobium;
   wherein the alloy is substantially free of toxic elements, said toxic elements being aluminum, manganese, vanadium, cobalt, nickel, molybdenum and chromium, except such amounts of said toxic elements as may occur as impurities in the alloy and as contaminants as a result of an alloying process, the amounts of said impurities and contaminants being insignificant to cause adverse effect on the patient's body.

2. The annuloplasty ring of claim 1, wherein said components include a core and a woven sleeve.

3. The annuloplasty ring of claim 1, wherein said metal alloy further includes an amount of zirconium sufficient to retard the transformation of beta.

4. The annuloplasty ring of claim 3, wherein the metal alloy includes from about 0.5 to about 20 wt. % zirconium.

5. The annuloplasty ring of claim 1, further including a hardened outer surface layer on at least a portion of said components, said layer formed on said components by a process selected from the group consisting of oxygen diffusion hardening, nitrogen diffusion hardening, physical vapor deposition, and chemical vapor deposition.

6. The annuloplasty ring of claim 3, further including a hardened outer surface layer on at least a portion of said components, said layer formed on said components by a process selected from the group consisting of oxygen diffusion hardening, nitrogen diffusion hardening, physical vapor deposition, and chemical vapor deposition.

7. The annuloplasty ring of claim 1, claim 3, claim 5 or claim 6, wherein surfaces of said components that come into contact with body tissue or fluid are at least partially coated with a composition selected from the group consisting of anticoagulants, antimicrobial agents, antibiotics, and medicaments.

8. The annuloplasty ring of claim 1, claim 3, claim 5 or claim 6, further including a lower friction wear-resistant outer surface layer on at least a portion of said components, said lower friction wear-resistant outer surface layer produced by a process selected from the group consisting of boronation and silver doping.

9. The annuloplasty ring of claim 3, wherein the metal alloy includes about 74 wt. % titanium, about 13 wt. % niobium, and about 13 wt. % zirconium.

10. The annuloplasty ring of claim 3, wherein the metal alloy includes titanium, from about 10 to about 20 wt. % niobium, and up to about 20 wt. % zirconium.

11. The annuloplasty ring of claim 3, wherein the metal alloy includes titanium, from about 35 to about 50 wt. % niobium, and up to about 20 wt. % zirconium.

12. A annuloplasty ring for implantation in living body tissue of a patient, the annuloplasty ring having enhanced biocompatibility, comprising:
   components at least partially fabricated from a metal alloy comprising:
   (i) titanium; and
   (ii) niobium and tantalum, wherein the combined wt. % of niobium and tantalum is from about 10 to about 20 wt. % or from about 35 to about 50 wt. %;
   wherein the alloy is substantially free of toxic elements, said toxic elements being aluminum, manganese, vanadium, cobalt, nickel, molybdenum and chromium, except such amounts of said toxic elements as may occur as impurities in the alloy and as contaminants as a result of an alloying process, the amounts of said impurities and contaminants being insignificant to cause adverse effect on the patient's body.

13. The annuloplasty ring of claim 12, wherein said components include a core and a woven sleeve.

14. The annuloplasty ring of claim 12, wherein said alloy further includes an amount of zirconium sufficient to retard the transformation of beta.

15. The annuloplasty ring of claim 14, wherein the metal alloy includes from about 0.5 to about 20 wt. % zirconium.

16. The annuloplasty ring of claim 12, further including a hardened outer surface layer on at least a portion of said components, said layer formed on said components by a process selected from the group consisting of oxygen diffusion hardening, nitrogen diffusion hardening, physical vapor deposition, and chemical vapor deposition.

17. The annuloplasty ring of claim 14, further including a hardened outer surface layer on at least a portion of said components, said layer formed on said components by a process selected from the group consisting of oxygen diffusion hardening, nitrogen diffusion hardening, physical vapor deposition, and chemical vapor deposition.

18. The annuloplasty ring of claim 12, claim 14, claim 16 or claim 17, wherein surfaces of said components that come into contact with body tissue or fluid are at least partially coated with a composition selected from the group consisting of anticoagulants, antimicrobial agents, antibiotics, and medicaments.

19. The annuloplasty ring of claim 12, claim 14, claim 16 or claim 17, further including a lower friction wear-resistant outer surface layer on at least a portion of said components, said lower friction wear-resistant outer surface layer produced by a process selected from the group consisting of boronation and silver doping.

* * * * *